US00PP17533P2

(12) United States Plant Patent
Smith

(10) Patent No.: US PP17,533 P2
(45) Date of Patent: Mar. 27, 2007

(54) ***CHRYSANTHEMUM* PLANT NAMED 'YOGWENDOLYN'**

(50) Latin Name: *Chrysanthemum×morifolium*
Varietal Denomination: Yogwendolyn

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 53 days.

(21) Appl. No.: 11/157,308

(22) Filed: Jun. 21, 2005

(51) Int. Cl.
*A01H 5/00* (2006.01)

(52) U.S. Cl. ..... Plt./294

(58) Field of Classification Search ..... Plt./294
See application file for complete search history.

*Primary Examiner*—Anne Marie Grunberg
*Assistant Examiner*—Georgia Helmer
(74) *Attorney, Agent, or Firm*—C. A. Whealy

(57) ABSTRACT

A new and distinct cultivar of *Chrysanthemum* plant named 'Yogwendolyn', characterized by its upright and somewhat outwardly spreading plant habit; freely branching habit; dense and full plant habit; uniform and freely flowering habit; daisy-type inflorescences with elongated oblong-shaped ray florets; white-colored ray florets; and natural season flowering in early September in the Northern Hemisphere.

2 Drawing Sheets

Botanical designation: *Chrysanthemum×morifolium.*
Cultivar denomination: 'Yogwendolyn'.

BACKGROUND OF THE INVENTION

The present invention relates to a new and distinct cultivar of *Chrysanthemum* plant, botanically known as *Chrysanthemum×morifolium,* commercially known as a garden-type *Chrysanthemum* and hereinafter referred to by the name 'Yogwendolyn'.

The new cultivar is a product of a planned breeding program conducted by the Inventor in Gainesville and Alva, Fla. The objective of the breeding program is to create new garden-type *Chrysanthemum* cultivars having inflorescences with desirable inflorescence forms, attractive floret colors and good garden performance.

The new *Chrysanthemum* originated from a cross-pollination made in March, 2001 in Gainesville, Fla., of the *Chrysanthemum×morifolium* cultivar Atlantico, disclosed in U.S. Plant Pat. No. 11,606, as the female, or seed, parent with the *Chrysanthemum×morifolium* cultivar Tracy, disclosed in U.S. Plant Pat. No. 8,609, as the male, or pollen, parent. The new *Chrysanthemum* was discovered and selected by the Inventor as a single flowering plant within the progeny of the stated cross-pollination grown in a controlled environment in Alva, Fla. in September, 2001. The selection of this plant was based on its desirable inflorescence form, attractive floret coloration and good garden performance.

Asexual reproduction of the new cultivar by terminal vegetative cuttings in a controlled environment in Alva, Fla. since January, 2002, has shown that the unique features of this new *Chrysanthemum* are stable and reproduced true to type in successive generations.

SUMMARY OF THE INVENTION

The cultivar Yogwendolyn has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yogwendolyn'. These characteristics in combination distinguish 'Yogwendolyn' as a new and distinct cultivar:

1. Upright and somewhat outwardly spreading plant habit.
2. Freely branching habit; dense and full plants.
3. Uniform and freely flowering habit.
4. Daisy-type inflorescences with elongated oblong-shaped ray florets.
5. White-colored ray florets.
6. Natural season flowering in early September in the Northern Hemisphere.

In side-by-side comparisons conducted in Alva, Fla., plants of the new *Chrysanthemum* differed from plants of the female parent, the cultivar Atlantico, in the following characteristics:

1. Plants of the new *Chrysanthemum* were larger than plants of the cultivar Atlantico.
2. Plants of the new *Chrysanthemum* flowered about two weeks earlier than plants of the cultivar Atlantico when grown under natural season conditions.
3. Plants of the new *Chrysanthemum* had smaller inflorescences than plants of the cultivar Atlantico.
4. Plants of the new *Chrysanthemum* and the cultivar Atlantico differed in ray floret coloration as plants of the cultivar Atlantico had yellow bronze-colored ray florets.
5. Plants of the new *Chrysanthemum* had longer lasting inflorescences than plants of the cultivar Atlantico.

In side-by-side comparisons conducted in Alva, Fla., plants of the new *Chrysanthemum* differed from plants of the male parent, the cultivar Tracy, in the following characteristics:

1. Plants of the new *Chrysanthemum* were not as mounded as plants of the cultivar Tracy.

2. Plants of the new *Chrysanthemum* flowered about ten days earlier than plants of the cultivar Tracy.
3. Plants of the new *Chrysanthemum* flowered more uniformly than plants of the cultivar Tracy.
4. Plants of the new *Chrysanthemum* had smaller inflorescences than plants of the cultivar Tracy.

Plants of the new *Chrysanthemum* can be compared to plants of the *Chrysanthemum* cultivar Stephanie, disclosed in U.S. Plant Pat. No. 9,445. In side-by-side comparisons conducted in Alva, Fla., plants of the new *Chrysanthemum* differed from plants of the cultivar Stephanie in the following characteristics:

1. Plants of the new *Chrysanthemum* were stronger, slightly larger and more rounded than plants of the cultivar Stephanie.
2. Plants of the new *Chrysanthemum* had lighter green-colored foliage than plants of the cultivar Stephanie when grown under natural season conditions.
3. Plants of the new *Chrysanthemum* flowered two to three days earlier than plants of the cultivar Stephanie when grown under natural season conditions.
4. Plants of the new *Chrysanthemum* had smaller inflorescences than plants of the cultivar Stephanie.

Plants of the new *Chrysanthemum* can also be compared to plants of the *Chrysanthemum* cultivar Starlet White, not patented. In side-by-side comparisons conducted in Alva, Fla., plants of the new *Chrysanthemum* differed from plants of the cultivar Starlet White in the following characteristics:

1. Plants of the new *Chrysanthemum* were larger than plants of the cultivar Starlet White.
2. Plants of the new *Chrysanthemum* had larger inflorescences than plants of the cultivar Starlet White.

BRIEF DESCRIPTION OF THE PHOTOGRAPHS

The accompanying photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph on the first sheet comprises a side perspective view of a typical flowering plant of 'Yogwendolyn' grown in a container.

The photograph on the second sheet comprises a close-up view of typical inflorescences of the cultivar 'Yogwendolyn'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Leamington, Ontario, Canada during the late summer and early fall in an outdoor nursery under conditions and practices which approximate those generally used in commercial garden-type *Chrysanthemum* production. One cutting was planted in a 15.25-cm container in mid-July, 2004. Plants were grown under natural season conditions. During the production of the plants, temperatures ranged from 10° to 32° C. Measurements and numerical values represent averages for typical flowering plants.

Botanical classification: *Chrysanthemum*×*morifolium* cultivar Yogwendolyn.

Commercial classification: Daisy-type garden *Chrysanthemum*.

Parentage:

*Female, or seed, parent.*—*Chrysanthemum*× *morifolium* cultivar Atlantico, not patented.

*Male, or pollen, parent(s).*—*Chrysanthemum*× *morifolium* cultivar Tracy, disclosed in U.S. Plant Pat. No. 8,609.

Propagation:

*Type.*—Terminal vegetative cuttings.

*Time to initiate roots.*—About four days at 21° C.

*Time to produce a rooted cutting.*—About ten to twelve days at 21° C.

*Root description.*—Fine, fibrous; white in color.

*Rooting habit.*—Freely branching.

Plant description:

*Plant form/growth habit.*—Perennial herbaceous daisy-type garden *Chrysanthemum*. Inverted triangle with mounded crown. Stems initially upright, then somewhat outwardly spreading habit. Freely branching with about twelve primary branches with lateral branches potentially forming at every node. Vigorous growth habit.

*Plant height.*—About 25 cm.

*Plant diameter.*—About 38 cm.

*Lateral branches.*—Length: About 23 cm. Diameter: About 6.5 mm. Internode length: About 1.3 cm. Aspect: Upright and outwardly spreading. Texture: Pubescent. Color: 146A.

*Foliage description.*—Leaf arrangement: Alternate. Length: About 4 cm. Width: About 3.3 cm. Apex: Mucronate. Base: Mostly truncate. Margin: Palmately lobed, sinuses mostly divergent. Texture, upper surface: Slightly pubescent. Texture, lower surface: Pubescent; veins prominent. Color: Developing and fully expanded foliage, upper surface: More green than 147A. Developing and fully expanded foliage, lower surface: Close to 147A. Venation, upper surface: More green than 147A. Venation, lower surface: Close to 147A. Petiole length: About 1.3 cm. Petiole diameter: About 2.5 mm. Petiole color, upper and lower surfaces: Close to 146A.

Inflorescence description:

*Appearance.*—Daisy-type inflorescence form with elongated oblong-shaped ray florets. Inflorescences borne on terminals above foliage, arising from leaf axils. Ray florets developing acropetally on a capitulum. About twelve inflorescences per lateral branch.

*Flowering response.*—Under natural season conditions, plants flower in early September in the Northern Hemisphere.

*Inflorescence bud (before showing color).*—Height: About 6 mm. Diameter: About 7 mm. Shape: Oblate. Color (lower surface of phyllaries): Between 139A and 147A.

*Inflorescence size.*—Diameter: About 3.7 cm. Depth (height): About 1.4 cm. Disc diameter: About 1.2 cm. Receptacle diameter: About 7.5 mm.

*Ray florets.*—Shape: Elongated oblong. Length: About 1.7 cm. Width: About 6 mm. Corolla tube length: About 3 mm. Corolla tube diameter: About 1 mm. Apex: Acute to rounded. Margin: Fused. Texture:

Smooth, glabrous; satiny. Surface: Concave to mostly flat. Orientation: Initially upright, then about 60° from vertical. Number of ray florets per inflorescence: About 46 in about two to three whorls. Color: When opening and fully opened, upper surface: Close to 155D. When opening and fully opened, lower surface: Close to 155D.

*Disc florets.*—Shape: Tubular, elongated. Length: About 4.5 mm. Width, apex: About 2 mm. Width, base: About 1 mm. Number of disc florets per inflorescence: About 160. Color: Immature: Close to 9A. Mature: Apex: Close to 9A. Mid-section: Close to 144B. Base: Close to 155D.

*Phyllaries.*—Quantity per inflorescence: About 20. Length: About 8 mm. Width: About 3 mm. Shape: Ligulate. Apex: Acute. Base: Truncate. Margin: Entire. Texture, upper surface: Smooth, waxy. Texture, lower surface: Pubescent. Color, upper surface: More green than 146A. Color, lower surface: Between 139A and 147A.

*Peduncle.*—Length: First peduncle; About 6.3 cm. Fourth peduncle: About 7.9 cm. Diameter: About 1.5 mm. Strength: Strong. Aspect: About 30° from vertical. Texture: Pubescent. Color: Close to 146A.

*Reproductive organs.*—Androecium: Present on disc florets only. Anther length: Less than 1 mm. Anther color: Close to 9A to 12A. Amount of pollen: None observed. Gynoecium: Present on both ray and disc florets. Style length: About 5 mm. Style color: Close to 154A. Stigma color: Close to 9A.

*Seed/fruit.*—Seed and fruit production has not been observed.

Disease/pest resistance: Plants of the new *Chrysanthemum* have not been shown to be resistant to pathogens and pests common to *Chrysanthemums.*

Garden performance: Plants of the new *Chrysanthemum* have been observed to be tolerant to rain, wind and temperatures ranging from 0° to more than 38° C.

It is claimed:

1. A new and distinct cultivar of *Chrysanthemum* plant named 'Yogwendolyn', as illustrated and described.

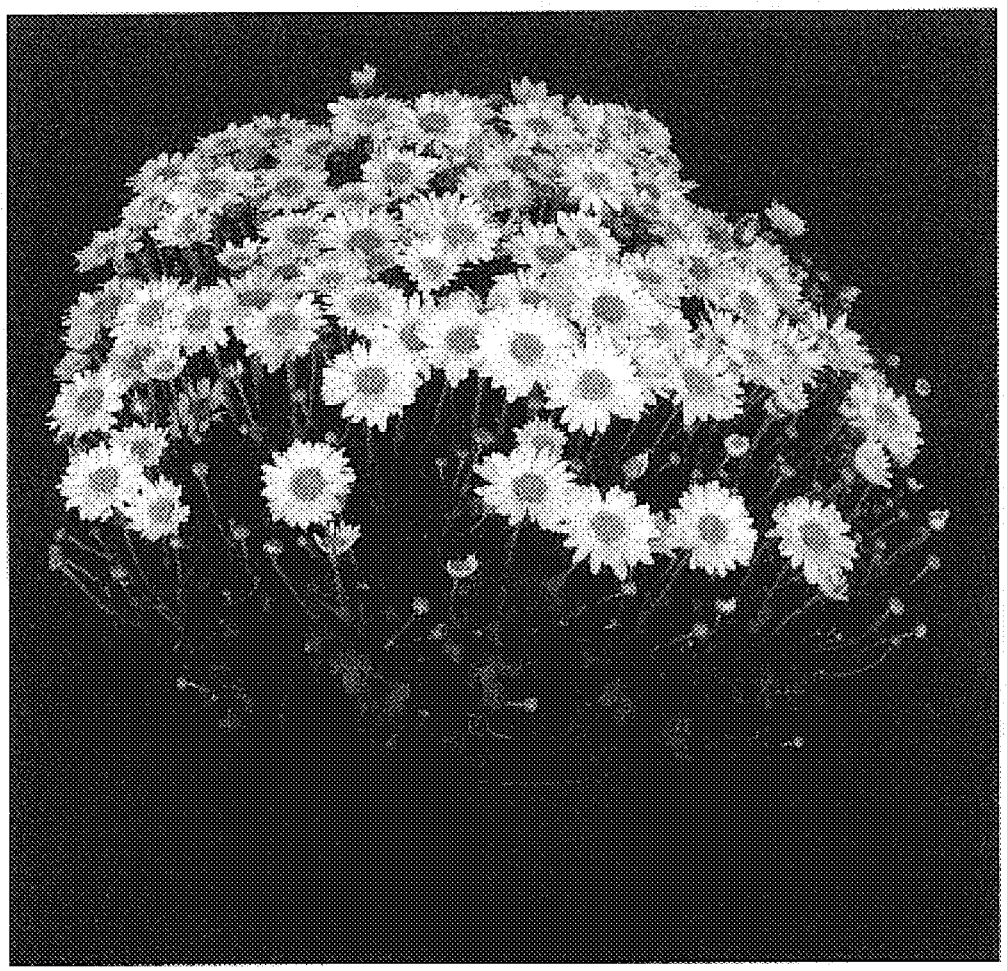

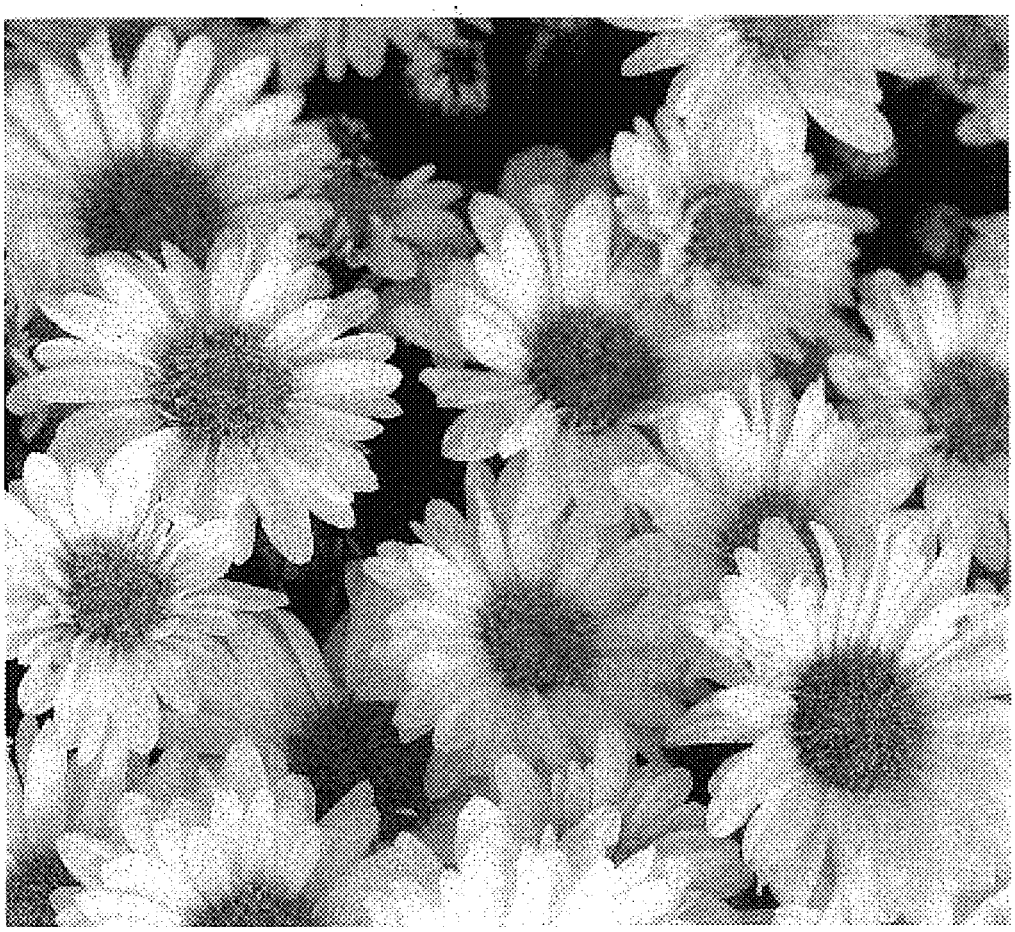

* * * * *